(12) United States Patent
Efremkin

(10) Patent No.: US 9,694,200 B2
(45) Date of Patent: *Jul. 4, 2017

(54) APPARATUS AND METHOD FOR TREATMENT OF FOOT AND NAIL DISEASES

(71) Applicant: Pavel V. Efremkin, Ardsley, NY (US)

(72) Inventor: Pavel V. Efremkin, Ardsley, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/168,896

(22) Filed: May 31, 2016

(65) Prior Publication Data

US 2016/0271414 A1 Sep. 22, 2016

Related U.S. Application Data

(62) Division of application No. 14/216,995, filed on Mar. 17, 2014, now Pat. No. 9,375,586.

(Continued)

(51) Int. Cl.
| | |
|---|---|
| *A61N 5/06* | (2006.01) |
| *A61H 35/00* | (2006.01) |
| *A61F 7/00* | (2006.01) |
| *A61K 31/5375* | (2006.01) |
| *A61K 33/14* | (2006.01) |

(Continued)

(52) U.S. Cl.
CPC ............ *A61N 5/062* (2013.01); *A61F 7/0085* (2013.01); *A61H 35/006* (2013.01); *A61K 31/5375* (2013.01); *A61K 33/14* (2013.01); *A61M 35/00* (2013.01); *A61M 37/0092* (2013.01); *A61N 1/40* (2013.01); *A61N 5/022* (2013.01); *A61N 5/0616* (2013.01); *A61N 5/0624* (2013.01); *A61B 2018/00452* (2013.01); *A61F 2007/0045* (2013.01); *A61F 2007/0046* (2013.01); *A61M 2037/0007* (2013.01); *A61M 2202/0468* (2013.01); *A61M 2230/005* (2013.01); *A61N 2005/067* (2013.01); *A61N 2005/0626* (2013.01); *A61N 2005/0645* (2013.01); *A61N 2005/0652* (2013.01);

(Continued)

(58) Field of Classification Search
None
See application file for complete search history.

(56) References Cited

U.S. PATENT DOCUMENTS

| | | | | | |
|---|---|---|---|---|---|
| 3,097,650 | A | * | 7/1963 | Mills .......................... | A61F 7/10 607/87 |
| 4,331,137 | A | * | 5/1982 | Sarui .................... | A61M 11/005 128/200.16 |

(Continued)

*Primary Examiner* — Lynsey Crandall
*Assistant Examiner* — Manolis Pahakis
(74) *Attorney, Agent, or Firm* — Lawrence G. Fridman, Esq.; Feigin & Fridman, LLC

(57) ABSTRACT

A method and apparatus for treatment of fungal infections and/or other foot skin disorders, comprises a shoe-type housing having a substantially hollow interior forming a treatment chamber, a supporting platform disposed within the hollow chamber; so that a foot of a patient positioned within the treatment chamber is supported by the platform, so that nails are disposed at the lower level of the front part of the chamber, whereas the heel of the foot is being elevated a rear part thereof. A delivery and control assembly for the aqueous solution is provided. At least one light delivery arrangement is disposed within or in the vicinity of the treatment chamber.

10 Claims, 6 Drawing Sheets

Related U.S. Application Data

(60) Provisional application No. 61/799,896, filed on Mar. 15, 2013.

(51) Int. Cl.
*A61M 35/00* (2006.01)
*A61M 37/00* (2006.01)
*A61N 1/40* (2006.01)
*A61N 5/02* (2006.01)
*A61N 5/067* (2006.01)
*A61B 18/00* (2006.01)

(52) U.S. Cl.
CPC ............... *A61N 2005/0654* (2013.01); *A61N 2005/0659* (2013.01); *A61N 2005/0661* (2013.01)

(56) References Cited

U.S. PATENT DOCUMENTS

| | | | | |
|---|---|---|---|---|
| 5,358,503 A * | 10/1994 | Bertwell | A61N 5/0616 | 257/E25.028 |
| 5,616,140 A * | 4/1997 | Prescott | A61N 5/06 | 606/10 |
| 6,156,028 A * | 12/2000 | Prescott | A61B 18/20 | 36/1 |
| 6,317,903 B1 * | 11/2001 | Brunelle | A61H 33/02 | 4/541.1 |
| 6,443,978 B1 * | 9/2002 | Zharov | A61N 5/0616 | 606/13 |
| 6,743,249 B1 * | 6/2004 | Alden | A61N 5/0601 | 606/1 |
| 7,100,615 B1 * | 9/2006 | Kert | A61N 5/0616 | 128/898 |
| 2001/0028227 A1 * | 10/2001 | Lys | A61N 5/0616 | 315/317 |
| 2001/0053421 A1 * | 12/2001 | Schaller | A41D 19/0058 | 427/557 |
| 2002/0029071 A1 * | 3/2002 | Whitehurst | A61N 5/0613 | 607/88 |
| 2002/0173781 A1 * | 11/2002 | Cense | A61B 18/203 | 606/9 |
| 2003/0032950 A1 * | 2/2003 | Altshuler | A61B 17/545 | 606/9 |
| 2003/0050674 A1 * | 3/2003 | Joshi | A61H 35/00 | 607/50 |
| 2003/0060813 A1 * | 3/2003 | Loeb | A61B 18/24 | 606/17 |
| 2004/0044384 A1 * | 3/2004 | Leber | A61N 5/0619 | 607/88 |
| 2005/0254993 A1 * | 11/2005 | Tanaka | A61M 35/00 | 422/33 |
| 2006/0167532 A1 * | 7/2006 | Parker | A61N 5/0616 | 607/88 |
| 2006/0206173 A1 * | 9/2006 | Gertner | A61N 5/0616 | 607/88 |
| 2007/0027481 A1 * | 2/2007 | Weinfield | A61F 7/02 | 607/1 |
| 2007/0288071 A1 * | 12/2007 | Rogers | A61N 5/062 | 607/88 |
| 2009/0018622 A1 * | 1/2009 | Asvadi | A61N 5/0621 | 607/91 |
| 2009/0062890 A1 * | 3/2009 | Ugajin | A61F 7/034 | 607/104 |
| 2009/0143842 A1 * | 6/2009 | Cumbie | A61N 5/0616 | 607/88 |
| 2010/0022941 A1 * | 1/2010 | Pelkus | A61G 10/02 | 604/20 |
| 2010/0324611 A1 * | 12/2010 | Deming | A43B 3/0005 | 607/2 |
| 2011/0098741 A1 * | 4/2011 | Pfeiffer | A61H 9/0078 | 606/201 |
| 2011/0137268 A1 * | 6/2011 | Thomason | A61M 35/003 | 604/291 |
| 2011/0208116 A1 * | 8/2011 | Nakamura | A61H 33/02 | 604/24 |
| 2012/0232467 A1 * | 9/2012 | Nakamura | A61G 10/026 | 604/24 |
| 2012/0283622 A1 * | 11/2012 | Nath | A61N 5/0616 | 604/20 |
| 2014/0074010 A1 * | 3/2014 | Veres | A61N 5/06 | 604/20 |
| 2014/0276257 A1 * | 9/2014 | Santa Maria | A61F 7/02 | 601/18 |

* cited by examiner

APPARATUS AND METHOD FOR TREATMENT OF FOOT AND NAIL DISEASES

REFERENCE TO RELATED APPLICATION

This Application is a Divisional of currently pending U.S. application Ser. No. 14/216,995 Filed: May 17, 2014, which claims priority of Provisional Application Ser. No. 61/799,896 filed Mar. 15, 2013. All above applications are incorporated herein by reference in their entirety.

BACKGROUND OF THE INVENTION

Skin and nail disorders affect all population at different stages of our life with increased level of incidence in the aging population. Many of such skin disorders are caused by a wide variety of different pathogens that reside on the skin and nails as well as in the deeper skin tissue. Such skin pathogens may include fungi, mold, parasites, bacteria, viruses and other microorganisms. There are different treatments, methods and techniques used to destroy or suppress such pathogens however mostly such treatments would affect one or few of such pathogens without affecting others or the treatment is only applied to a certain part of the foot for example like nails affected by onychomycosis leaving other foot skin untreated. However pathogens residing in other areas of foot skin often cause decease in other foot areas like mold or fungus on the foot skin can easy migrate to the nails. Therefore there is a strong need for a method and device that could integrate multiple treatments of foot skin and nails into a one complex treatment which will result in increased clinical efficacy and outcome for patients as well as it will provide for cost saving for the healthcare system overall.

It is estimated that up to 35 million Americans have onychomycosis, a condition relating to fungal infections of the toenails or fingernails. Onychomycosis is often caused by yeast, dermatophytes, or other molds, and represents approximately 50% of all nail disorders. Toenail infection accounts for approximately 80% of onychomycosis incidence, while fingernails are affected in about 20% of the cases. Dermatophytes are the most frequent cause of nail plate invasion, particularly in toenail onychomycosis. Discoloration, onycholysis, and accumulation of subungual debris and nail plate dystrophy characterize the disease. The disease adversely affects the quality of life of its victims, with subject complaints ranging from unsightly nails and discomfort with footwear, to more serious complications including secondary bacterial infections.

Many methods are known for the treatment of fungal infections, including use of oral and topical drugs. However, onychomycosis has proven to be resistant to most treatments. Nail fungal infections reside in an area difficult to access by conventional topical treatment and anti-fungal drugs cannot readily penetrate the nail plate to reach the infection sites under the nail as well into the nail matrix where infection is often resided therefore clinical efficacy of topical medications is low (20-25% estimated). Also onychomycosis has traditionally been treated by oral administration of anti-fungal drugs. However, the clinical efficacy of the treatment is still not complete (50-60% estimated) and there is a high rate of fungal infection recurrence and with multiple treatment courses patients developed resistant to the oral medication which further reduce the clinical efficacy. There is also known potential for serious side effects of such drugs. Recently significant interest has developed in the use of light irradiation by laser to destroy fungal material through superheating (coagulation) of soft tissue affected with fungus. Exposure of fungi to high temperatures inhibits their growth as well as cause their cell damage and death. This type of therapy using proper light parameters such as wavelength and pulse duration and high level of energy has shown a high clinical efficacy in fungal infection destruction. Light sources capable of emitting high energy in the infrared spectrum proved to be most efficient in eradicating of onychomycosys because high energy infrared radiation with optimum parameters can penetrate deep into skin tissue through the nail plate and into the nail bed as well as deep into the nail matrix coagulating fungal material often residing in these deep skin area. It also has the added benefit of avoiding side effects of oral drugs mentioned above and other systemic concerns for the patient. However delivering of high energy levels to the pathogen affected skin tissue may require efficient cooling mechanisms to remove heat build up in the skin tissue to prevent unwanted collateral damage and provide for a more comfortable treatment for a patient.

Thus, it has been a long felt and unsolved need for an apparatus and method for treatment of fungal infection disease of the lower and upper limbs, including, but not limited to toenails and fingernails that could integrate multiple treatments available now into a one complex treatment and which can be efficiently provided without threat of side effects.

In addition to nails fungal east and bacterial infection, including athlete's foot, mold, viruses, parasites, or other organisms or microorganisms can reside on the skin surface of lower and upper limbs causing chronic infections, which may result in development of wounds including chronic wounds. Some other serious skin disorders like psoriasis and others are common for the skin surface of lower and upper limbs as well. Therefore it is preferable that such method and apparatus will allow to treat in one treatment all or most of foot and hand skin deceases including but not limited to the nails fungal and bacterial infection not only on and under the nails but also on all areas of skin of the lower and upper limbs as well is that it can be used for treatment of wounds, psoriasis and other skin disorders.

SUMMARY OF THE INVENTION

The invention provides a method, means and apparatus to simultaneously or in one procedure treat multiple foot and hand skin and nail deceases. Further in the text skin should be understood as both skin and nail of the lower and upper limbs and other body areas if applicable. The method includes simultaneous or alternate application of some or all of the following steps:

Step One relates to application of energy radiation to selectively destroy, coagulate, or damage pathogen elements causing disorders of skin and nail with such energy radiation to include thermal radiation, electromagnetic radiation including but not limited to light, laser irradiation, electrical current, RF (radio frequency), microwave etc, ultrasonic, mechanical and other; with proper parameters such energy application may also stimulate a wound healing response including enhancing of colagenesis.

Step Two relates to washing of treated skin with aqueous solution which to include any type of aqueous solution containing substances capable of destroying skin pathogens and/or is used for treatment of wounds, psoriasis and other skin disorders. It should be noted however that in an alternate embodiment the step of washing can be conducted after the step of applying energy irradiation.

Step Three relates to the use of the aqueous solution as per above or special separate aqueous or gas substance as a cooling agent to remove heat build up in the skin tissue and nails caused by the application of energy radiation.

Step Four, which can be optional, relates to drying the aqueous solution applied in the Step Two and/or Three from the treated skin to prepare the skin for the application of energy radiation described in Step One to avoid absorption of such radiation in the aqueous solution which may reduce effect of energy irradiation or result in superficial overheating of the skin;

In one of the embodiments of the invention apparatus comprises a shoe-type housing having a substantially hollow interior forming a treatment chamber adapted to place a patient foot. At least one energy radiation/light delivery arrangement is disposed within or in the vicinity of the treatment chamber. A delivery and control assembly for the aqueous solution is provided allowing for full or partial washing of patient foot. A power and control unit providing operation of the apparatus in accordance with the steps described above is provided.

A supporting platform is disposed within the hollow chamber; so that a foot of a patient is conveniently positioned within the treatment chamber and supported by the platform. In the main embodiment of the chamber the support platform is positioned in such a way so that nails are disposed at the lower level of the front part of the chamber, whereas the heel of the foot is being elevated a rear part thereof. Such foot position allows for an option when only nails area is washed by the aqueous solution. An alternative platform positioning whereas the nails are being elevated and a rear part of the foot is put at the lower level thereof can be considered as well. In a situation when the apparatus may be used by multiple patients, for sanitary reasons and to prevent any cross contamination by pathogens the single use internal liner for the treatment chamber can be used. Alternatively the complete treatment chamber part of the apparatus can be designed as a single use disposable.

The energy radiation/light delivery outlets can be located in all areas of the treatment chamber to provide optimum irradiation of all skin areas. Different types of energy/light parameters can be used for irradiating different skin areas. For example for irradiation of nails for onychomycosis treatment the deep penetrating energy is preferred in order to coagulate fungal structures that may reside in nail bed or matrix. For other parts of the skin where pathogens are resided superficially a more superficially absorbed energy can be used to protect internal skin structures.

The aqueous solution in this invention delivers serves the following main objectives. First it may contain active ingredients that adversely effect skin pathogens and facilitate treatment and healing of different skin diseases. The aqueous solution delivery and control system allows for full or partial washing of patient foot depending on clinical objectives. It also provides for optimum time exposure of the skin to aqueous solution. Second, aqueous solution provides cooling of the nails and skin area treated with energy irradiation. This may be necessary to prevent unnecessary collateral overheating of the skin tissue and for patient comfort. Cooling elements are integrated into the apparatus design to control the aqueous solution temperature. In another embodiment there are two separate aqueous circulation loops, which may contain different types of aqueous solutions. In such case, first solution and first circulation loop will be used to circulate aqueous solution for washing foot skin. And the second circulation loop will fill the optically (energy) transparent pocket located near the nails area which is designed to provide contact cooling to the nails while being maximum transparent to the energy irradiation being delivered to the nail to treat onychomycosis. In another embodiment such optically (energy) transparent pocket can alternatively be filled with cooled gas or cryogen.

Because some energy irradiation may be absorbed in water or other aqueous solution used it is preferable that skin is dried before such energy irradiation is applied. For such purposes the apparatus may incorporate an air dryer subsystem designed to dry the skin by blowing air to it or by vacuuming an air stream from and through the treatment chamber.

Multiple sensors are installed within the treatment chamber to monitor different skin parameters including but not limited to temperature, melanin, hemoglobin, oxygen and water concentration in the skin, blood pressure and other heart related characteristic may be measured as well for better patient control. Using data collected by the monitoring sensors a power and control unit of the apparatus directs and controls operation of the apparatus in accordance with the treatment protocols.

Multiple embodiments of the treatment chamber can be used and adapted for different clinical applications. Some examples may include:

- a treatment chamber designed to accept just toes for onychomycosis treatment;
- a treatment chamber designed to accept hands or fingers;
- a treatment chamber designed to treat other parts of patient body skin where shape of such chamber design will be adapted to conveniently accept and locate such treatment site within such chamber. In such cases the energy radiation production arrangement, a delivery and control assembly for the aqueous solution and a power and control unit providing operation of the apparatus may be located separately from the treatment chamber and connected to it through a variety of connecting tubes, electrodes or optical fibers that will feed and control the corresponding outlets within the treatment chamber. It is possible that such treatment chambers can be adapted for single use, so as to be disposable for the purposes of patient's hygiene and safety. Multiple electronic and mechanical safety features are incorporated in the apparatus design including but not limited to preventing reuse of the disposable treatment chambers.

DETAILED DESCRIPTION OF THE INVENTION

Figure 1:
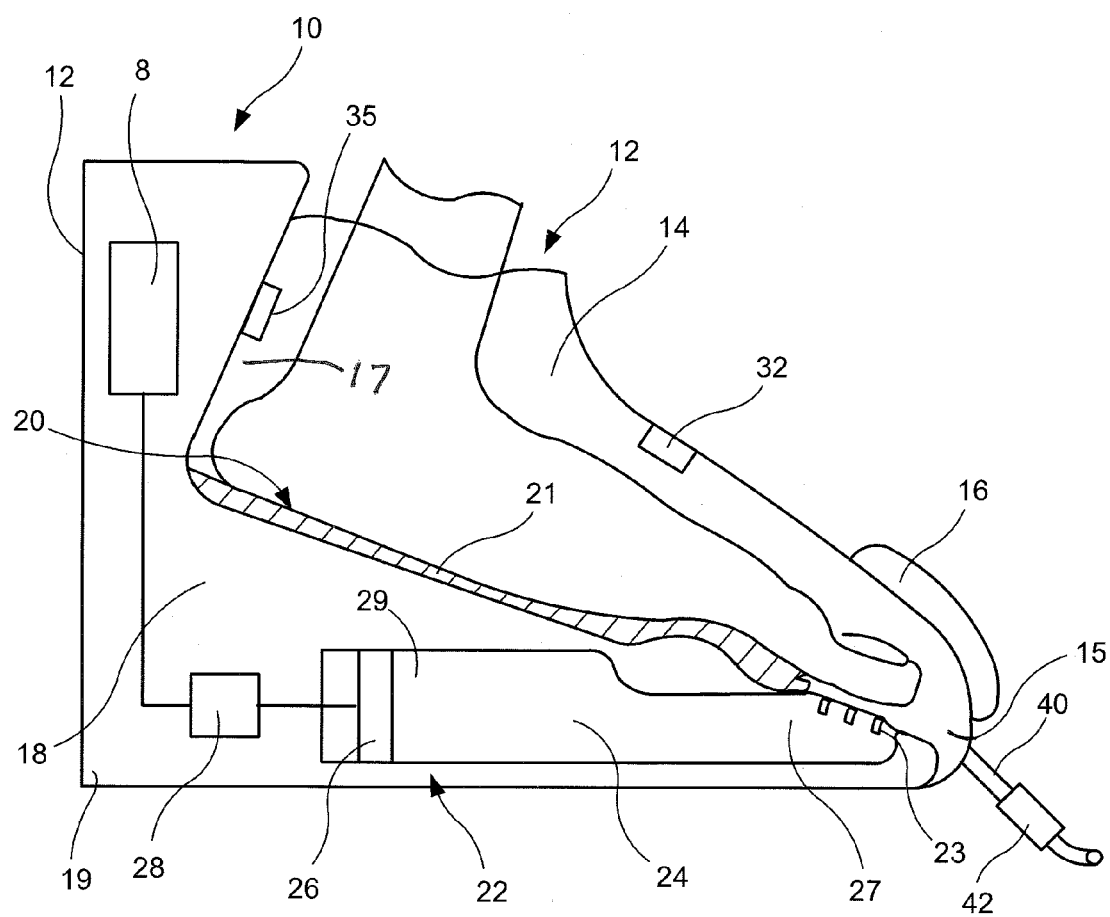
FIG. 1 is a schematic diagram illustrating one embodiment of an apparatus for treatment of foot and nail disease according to the invention.

The following terms are intended to have the following general meanings as they are used in the application.

Aqueous solution: any type of aqueous solution containing substances capable of eliminating skin pathogens including but not limited to fungus organisms, east and bacterial infection, including athlete's foot etc., treat psoriasis, acceleration of wound healing or treating any other skin disorders. Such substances are capable of either completely eliminating/destroying skin pathogens or substantially delaying reducing the rate of its growth. The treatment solutions include but not limited to the salt solution like sea water and etc., solutions containing Ethanol Alcohol, Iso-propyl alcohol, p-Chloro-o-benzylphenol, o-Phenylphenol, Potassium hydroxide, dimethylbenzylammonium chloride, Lactic acid, Hydrogen Peroxide, fluconazole, itraconazole, terbinafine amorolfine, methylphenols, creosols, and any other solutions that inhibits pathogens. Treatment solution may also include substances that promote healthy skin, wound healing and/or psoriasis treatment.

Light at any wavelengths can be absorbed by a skin or nails of the patient. Such wavelengths include wavelengths selected from the continuous electromagnetic spectrum such as ultraviolet ("UV"), visible, the infrared (near, mid and far) i.e. from approximately 300 nm to 12,000 nm, etc. The light may be produced by any suitable art-disclosed light emitting devices such as lasers, light emitting diodes ("LEDs"), incandescent sources, fluorescent sources, flash lamps or the like. The light can be pulsed or having a continuous mode. Under Light in this invention one can understand any energy radiation that can penetrate and affect the skin tissue including electromagnetic fields, radio frequency, and acoustic including ultra sound.

The light applied during the irradiating step of the method of the invention can be supplied by a single light emitting device or a plurality of light emitting devices. Any suitable art-disclosed light emitting device(s) such as lasers, light emitting diodes ("LEDs"), flash lamps, incandescent sources, fluorescent sources, germicidal light or the like may be used to provide the required wavelength(s). Lasers include any art-disclosed lasers such as solid state lasers, diode lasers, pulsed lasers, gas lasers, gas or vapor lasers, dye lasers, fibers lasers or diode pumped solid state lasers or the like. LEDs include any art-disclosed LEDs such as semiconductor LEDs, organic LEDS or a combination thereof. Fluorescent sources include any art-disclosed fluorescent sources such as fluorescent tubes, LED pumped fluorescent devices, cold cathode fluorescent panels or the like.

The light applied during the irradiating step of the method of the invention provides the required wavelength(s). Such wavelength(s) include wavelengths selected from the continuous electromagnetic spectrum such as ultra violet ("UV"), visible, the infrared (near, mid and far), etc. The wavelength, pulse duration/continuous mode, energy density to the skin or number and repetition rate of energy pulses is optimized to achieve optimal and selective absorption in the skin pathogens or skin components like melanin, oxy-hemoglobin or water as well as optimum depth of skin penetration for the best clinical efficacy outcome.

The time required for the step of exposing the infected area to an aqueous solution and the irradiating step of the method may vary depending on the existing conditions (e.g., type of the disease, the skin pathogens, the light source, the aqueous solution, the skin type, melanin concentration in the skin, hemoglobin concentration in the skin, moisture of the skin, temperature of the skin etc.). As to the irradiating step, a suitable duration will generally be from about 1 nanosecond to about 60 minutes. It is also possible and within the scope of the present invention for the light applied during the irradiating step of the therapy to be applied by a lower energy power for much longer durations (e.g., more than about 30 minutes to hours).

Referring now to the drawings, and more particularly to FIG. 1 illustrating therapeutic apparatus 10 of one embodiment of the invention which is adapted to treat toenail fungus and other medical conditions. In this embodiment the apparatus 10 is in the form of a shoe-type appliance 12 having a substantially hollow interior adapted to accommodate a treatment chamber 14. The chamber 14 extends between front 15 and rear 17 area is designed as a bath adapted to allow either one or both feet of a patient to fit comfortably and be immersed in the solution. The treatment chamber or the bath 14 is capable of holding amount of an aqueous solution required for a complete treatment of a patient. At least one energy or light source 16 is provided to allow irradiation of the foot over and around the toes and the nails. The energy source 16 is typically disposed in the vicinity of the front area 15 of the treatment chamber 14.

It should be obvious to a person skilled in the present art that the therapeutic apparatus of the invention can be also adapted for treatment of other parts of a body, which can be easily immersed into the solution contained within the chamber 14, for example, hands.

An inclined supporting platform 18 is disposed within the lower part of the interior of the apparatus. As illustrated in FIG. 1, a top surface 20 of the supporting platform is disposed at an acute angle to the bottom 19 of the apparatus. Other angles of inclination of the supporting platform to the bottom of the apparatus are within the scope of the invention. A foot of a patient is positioned within the treatment chamber 14, and supported by the platform 18 in such a manner that toenails of toes are disposed at a low level at the front area 15 of the chamber, whereas a heel of the foot is elevated at the rear area 17. In the illustrated embodiment of the invention a delivery and control system 22 for the aqueous solution is provided within the platform 18 at the vicinity of the bottom 19 of the apparatus. It should be noted however, that any alternate location of the system 22 inside or outside of the apparatus is within the scope of the invention. In the illustrated embodiment, the control system 22 consists of at least one cylinder 24 with a piston 26 slideably movable between proximal 27 and distal 29 ends thereof, and a control means or arrangement 28. The proximal end 27 of the cylinder is in fluid communication with the front area 15 of the treatment chamber 14. Control valve 23 is provided at the front area 15, so as to direct movement of the solution from the cylinder 24 into the treatment chamber 14. The control valve 23 is adapted to close communication with the treatment chamber 14 and the hollow interior of the apparatus when aqueous solution is reseeded. After being used during the treatment, the aqueous solution is discharged from the treatment chamber 14 through the discharged unit 40 which can be in the form of a pipeline initiated at the front area 15 of the treatment chamber. A filter 42 is provided at the discharge unit 40 to filter the discharged aqueous solution before it is being be re-circulated to the cylinder 24 or sent to an accumulator (not shown) for further use and/or storage.

As the piston 26 is activated, the aqueous solution through the front end 27 of the cylinder and the uni-directional valve arrangement 23 is delivered into the treatment chamber 14.

Figure 2:
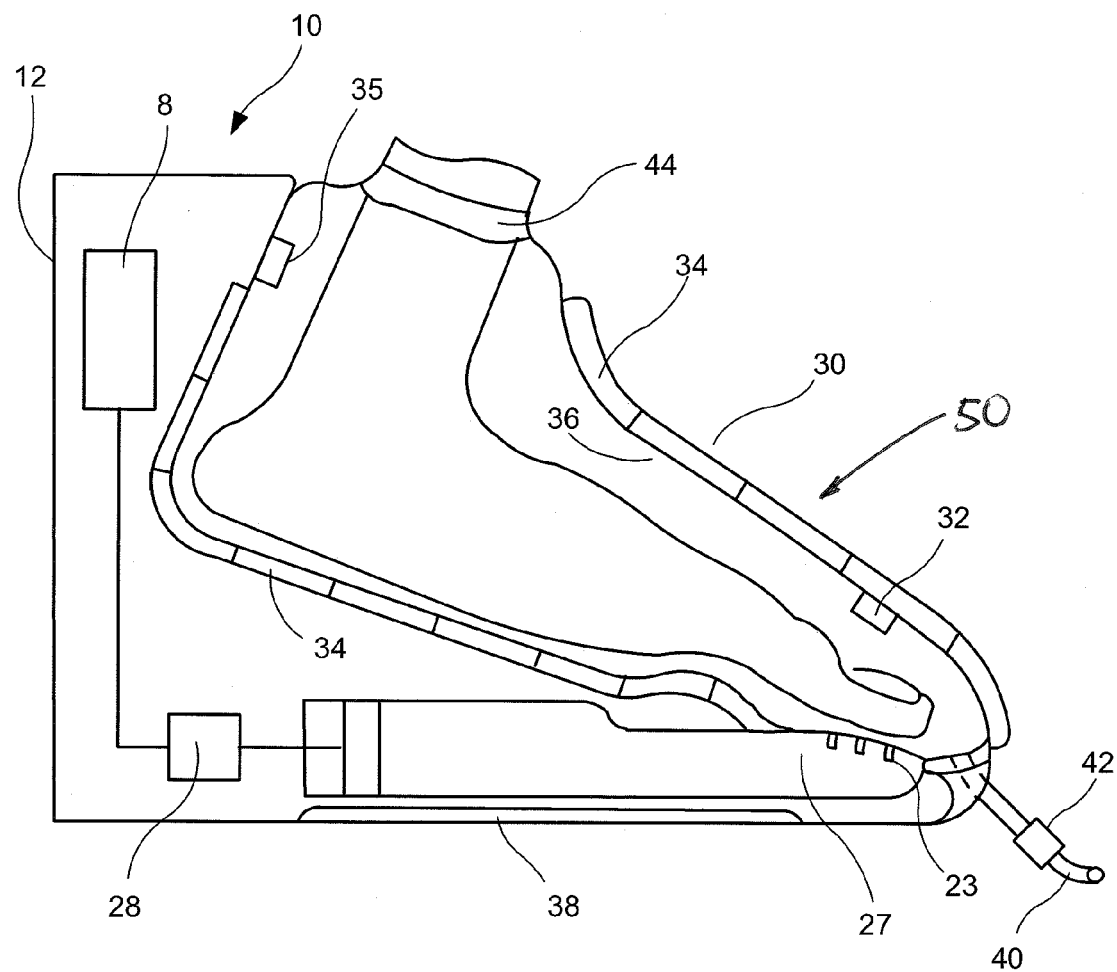
FIG. 2 is a schematic diagram of another embodiment of the apparatus of the invention.

During the treatment, a front of the foot with the toes and toenails, disposed at a low elevation of the front area 15, are submerged into the aqueous solution. The fungus infected toenails are washed, bathed within the aqueous solution, so that the aqueous solution flows around the infected areas. In this manner, the infected toenails are exposed to a greater degree to the medicated aqueous solution than the rest of the foot. Upon completion of this phase of the treatment, the aqueous solution is discharged from the treatment chamber 14 through the discharge unit 40 and the filter 42. As shown in FIG. 2, a resilient cuff 44 can be provided at a top portion of the treatment chamber 14 to surround an upper portion of an ankle and to prevent spillage of the aqueous solution.

In one embodiment of the invention, the top surface 20 of the platform supporting the foot is made from a resilient material. To enhance performance of the device, this resilient material is capable of adapting to a specific shape of the foot of the each individual patient. As illustrated in FIG. 1, a layer of gel 21 can be disposed below the resilient upper surface of the platform. In this manner, the top surface 20 of the supporting platform closely follows the shape of the foot facilitating substantial engagement therebetween. This feature is also important in the step of irradiation, which will be discussed with reference to the embodiment of FIG. 2, where energy sources or light elements are provided near the top surface of the platform.

Figure 3:
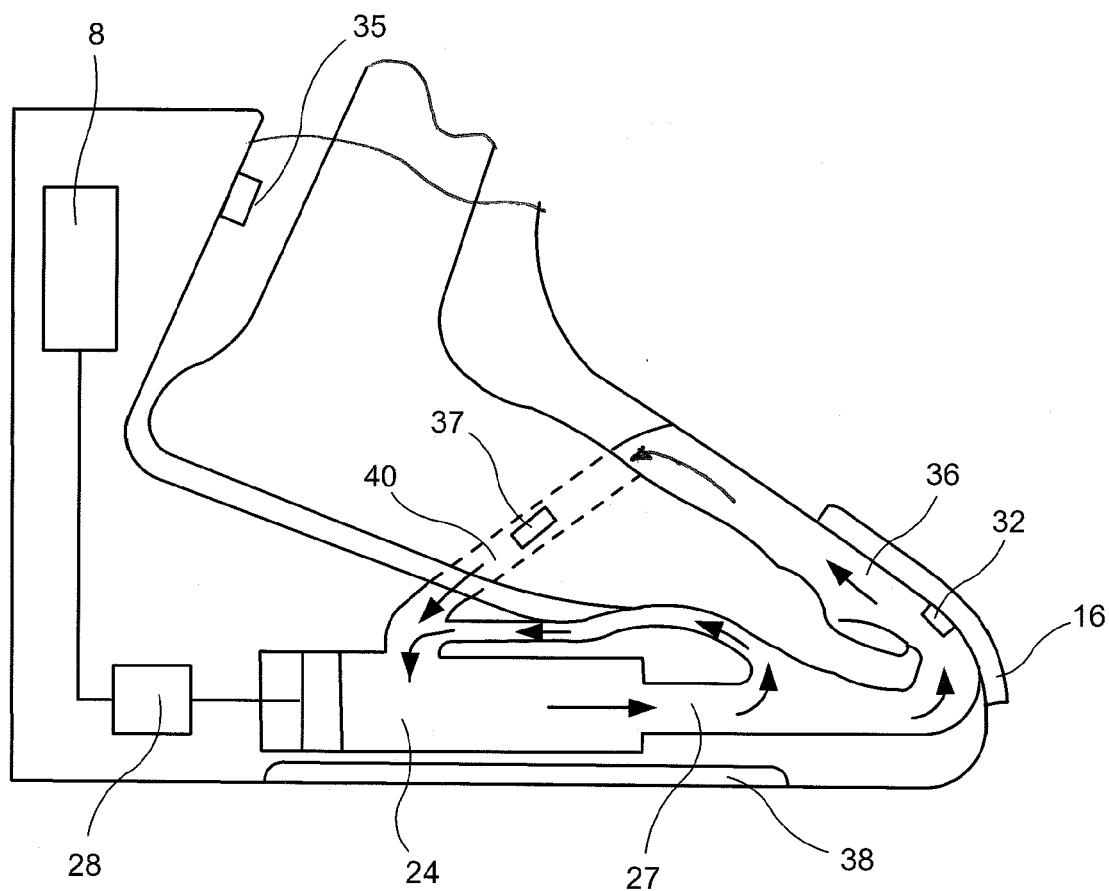
FIG. 3 is a schematic diagram of a further embodiment of the apparatus of the invention.
Figure 4:
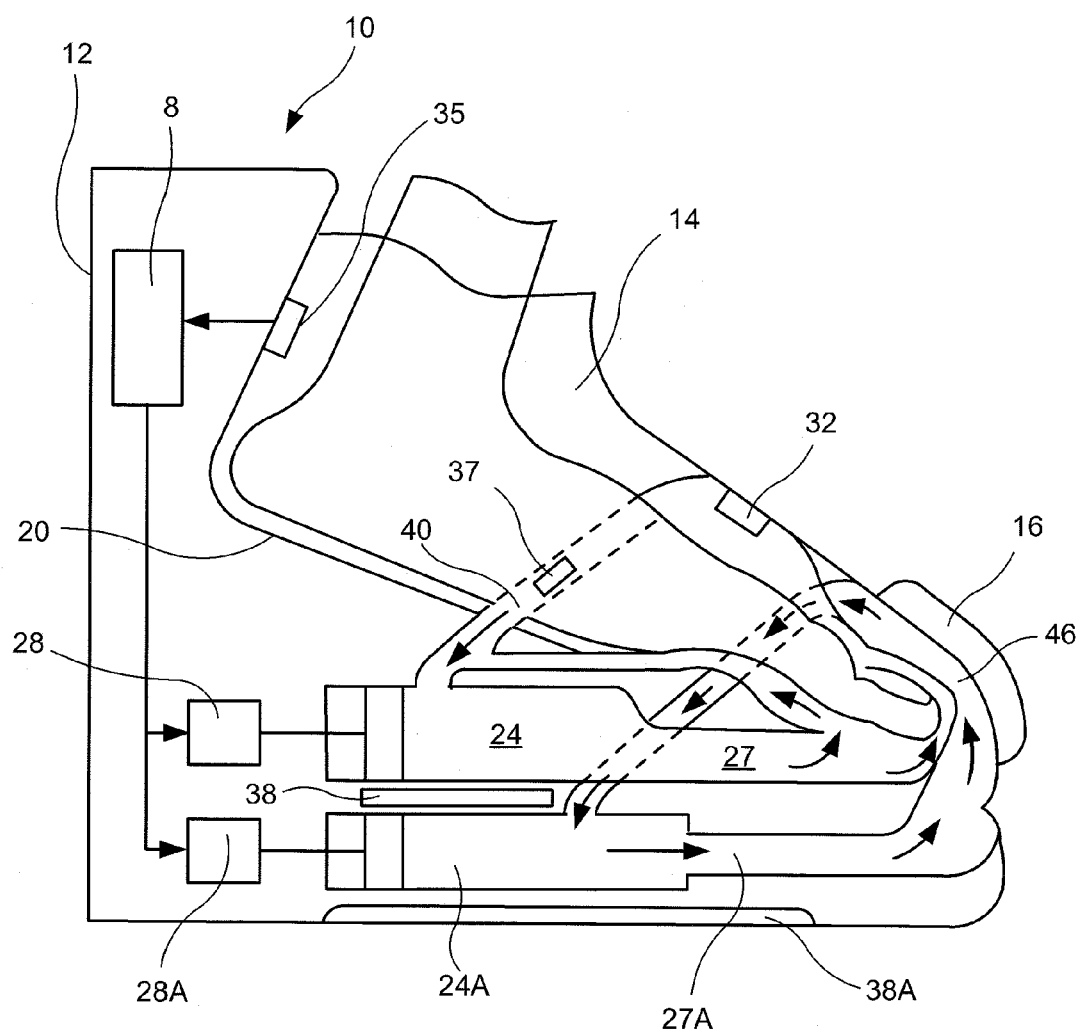
FIG. 4 is a schematic diagram of a still another embodiment of the apparatus of the invention.

As illustrated in FIGS. 2-4, a cooling arrangement in the form of at least one cooling plate 38, for example, is situated in the vicinity of the control system 22. One of the main functions of the cooling arrangement is to reduce the temperature in the treatment chamber including a temperature of the aqueous solution. Use of the cooling arrangement is especially beneficial in the embodiments where the aqueous solution is circulated within the apparatus between the treatment chamber having elevated temperature and the cylinder 24 (see FIGS. 3 and 4). As illustrated in FIGS. 3 and 4, in such systems, the cylinder or reservoir 24, the cooling plate 38 and the treatment chamber 14 are arranged as parts of the aqueous solution circulation loop 36. This arrangement allows the aqueous solution to circulate between the cylinder/reservoir 24, cooled by the cooling plate 38, to the interior of the treatment chamber 14, wherein a foot of a patient is positioned for treatment. As shown in FIG. 3, upon activation of the piston 26, the aqueous solution is being discharged from the cylinder 24 at the proximal end thereof 27 into the treatment chamber 14. After flowing around the infected areas of the foot, the aqueous solution through the circulation loop 36 is being recycled back to the cylinder 24. To facilitate efficient circulation of the solution, a circulation pump or any other similar conventional means 37 can be provided within the circulation loop 36.

Although, the cooling arrangement is in the form of the cooling plate 38 has been discussed hereinabove, it should be understood that any type of cooling arrangement provided to reduce a temperature of the aqueous solution within the treatment chamber is within the scope of the invention. For example, in an alternate embodiment of the invention, the entire supporting platform 18 is made from a resilient material, whereas an inner part of the platform is substantially hollow and filled with a cooling substance/liquid. The cooling substance cools the foot in general and the toes and toenails thereof in particular with the infected areas are treated by the apparatus and method of the invention.

In the embodiment of the apparatus shown in FIG. 4, a resilient light transparent pocket 46 filled with a cooling substance or cooling gel is provided at the front area of the chamber 14. In use the pocket 46 can adapt to the shape of the toes and toenails for a better cooling and better transmission of the light energy. The system of this embodiment is formed with at least two sets of cylinders or reservoirs 24 and 24A. The purpose of the cylinder 24 is similar to the analogous cylinders of the above-discussed embodiments, so as to provide delivery and/or circulation of the aqueous solution within the treatment chamber 14. The main objective of the reservoir 24A is to provide delivery and circulation of the cooling fluid within the auxiliary circulation loop 46. After being discharge from the reservoir 24A, the cooling fluid circulates within the light transparent pocket 46 and cools the nails area, so as to make application of irradiation energy to the nails area safer and more comfortable. The embodiment of FIG. 4 is formed with two cooling arrangements 38 and 38A. The cooling arrangement or cooling plate 38 is located in the vicinity of the cylinder 24 and provided to reduce the temperature of the solution delivered the treatment chamber 14. On the other hand the purpose of the cooling plate 38A positioned near the cylinder 24A is to reduce the temperature of the cooling solution circulating within an auxiliary circulation loop 46 adapted to cool the toe nail treatment area.

Figure 5:
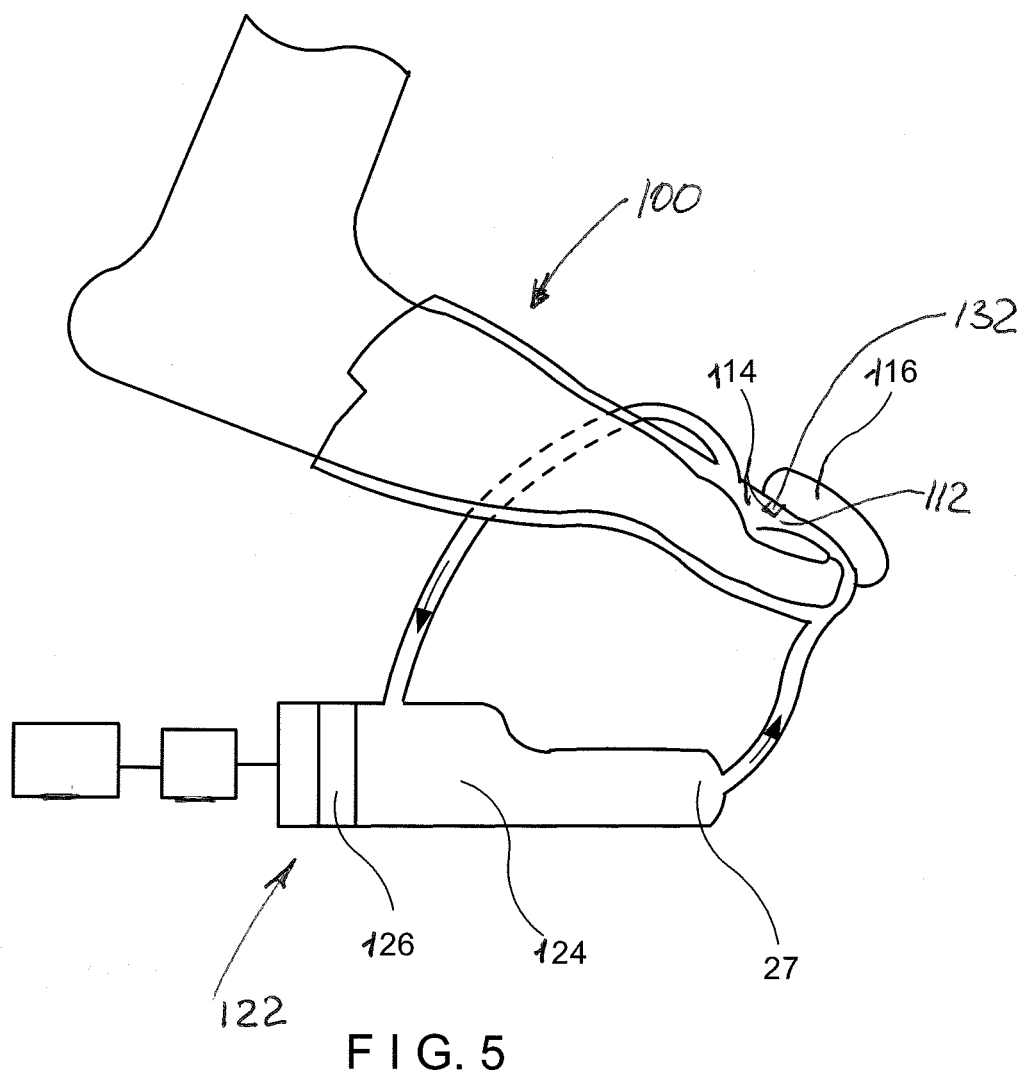
FIG. 5 is a schematic diagram of a further embodiment of the apparatus of the invention.

FIG. 5 illustrates a further embodiment of the apparatus 100 of the invention. In this embodiment, the body of the apparatus extends from the toes to about the middle of the foot with a limited treatment chamber 114 adapted to accommodate the foot front area including toes and toenails. The treatment chamber 114 includes a toe region 112 that surrounds the toes of a foot of a patient inserted thereinside. In some embodiments, toe region tapers from the inner area of the chamber to the outer area of the chamber such that it generally follows the contour of a human foot where larger toes exist at the inside of the foot, and the foot tapers to smaller toes on the outside. This can be functionally advantageous as the treatment chamber more closely conforms to the shape of the human foot. However, of ordinary skill in the art should appreciate that various shapes for toe region are within the scope of the invention.

Although, the apparatus 100 is formed with the treatment chamber 114 adapted to accommodate various sizes of human foot, an apparatus with a custom-formed treatment chamber designed to accommodate a custom foot configurations of a specific patient is within the scope of the invention. Such custom configured chambers are especially useful for patients with substantial foot deformities, as well as invalids having a part of a foot being removed, etc.

The apparatus of the embodiment illustrated in FIG. 5 is typically made from a resilient material such as rubber, for example. At least one energy light source 116 is provided at the proximal end of the chamber for irradiation of the foot in general and the toes and nails specifically. A tightening arrangement, such as a cuff 44 for example (see FIG. 2), can be formed at the distal end of the chamber to facilitate tight connection between the apparatus and the foot of the patient and to prevent leakage of the aqueous solution from the treatment chamber.

In the embodiment of FIG. 5, the delivery and control system 122 for the aqueous solution is situated outside of the apparatus. Similar to the above-discussed embodiments, the liquid control system 122 may include a cylinder 124 with a piston 126 movable thereinside. During the treatment, the front of the foot, including the toenails is submerged within the aqueous solution provided within the treatment chamber. A sensor 132 can be provided within the treatment chamber to further control the treatment process.

The resilient material used for manufacturing of the apparatus 100 is impermeable to the aqueous solution. In view of the relatively low cost of production, the apparatus is disposable in nature. The apparatus is convenient for specific treatment sessions arranged for particular patients. The control system 122 positioned outside of the apparatus is reusable and can disconnected from the treatment chamber 114 upon completion of the prescribed treatment. If needed, the control system 122 can be re-connected to another unit. Such arrangement provides substantial cost saving to an operator.

Figure 6A:
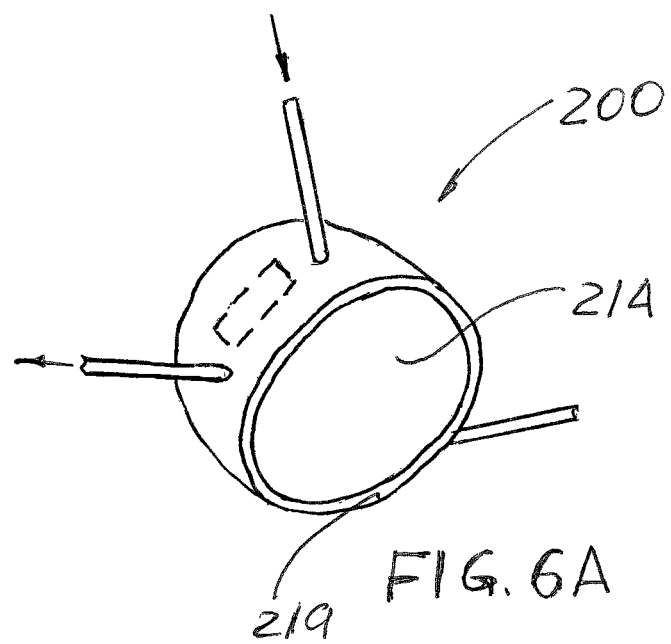
FIGS. 6A and 6B are schematic diagrams of an alternate embodiment of the apparatus of the invention.
Figure 6B:
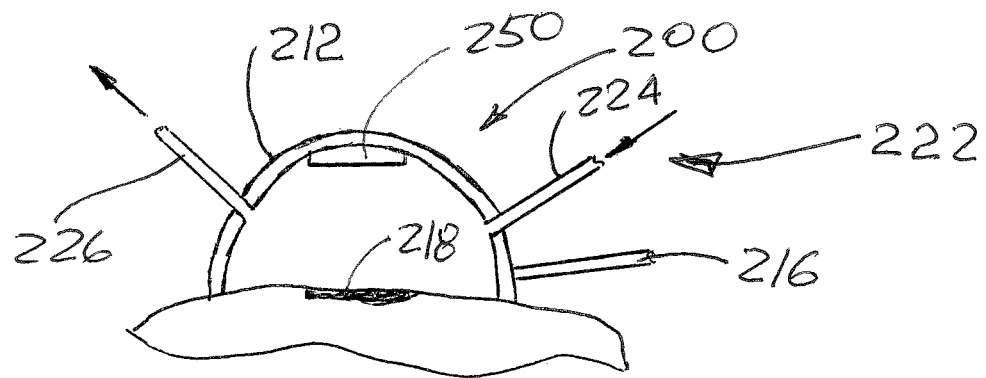

As indicated above, multiple embodiments of the apparatus of the invention including various treatment chambers can be used and adapted for different clinical applications. FIGS. 6A and 6B show the embodiment of the apparatus 200 of the invention provided for treatment of wounds and skin conditions 218 practically at any part of human body. The body 212 of the apparatus has a semi-spherical configuration with a hollow treatment chamber 214 formed thereinside. A vacuum arrangement 216 is provided to create a vacuum within a hollow space 219 formed between the walls of the treatment chamber 214, which are in contact with the skin. This arrangement facilitates better engagement between outer periphery of the body and the skin area to be treated. A delivery and control system 222 for the aqueous solution consisting of inlet 224 and outlet ports 226 is provided. A radiation energy source 250 is disposed within the chamber 214.

The light delivery arrangement 50 of the present invention includes a light source, an energy source in power communication to the light source; and a controller that controls amount and/or duration of light to be applied to the patient by the light source and sensors 32, 35 to measure skin/nails characteristics.

As discussed above, the light source can be any suitable art-disclosed light emitting device(s) such as lasers, LEDs, incandescent sources, fluorescent sources, or the like may be used to provide the required wavelength(s). A light source can be a visible infrared light generated by any conventional sources, including light bulbs, impulseable laser as well as the devices capable of absorbing and concentrating the sunlight.

In the embodiment of the invention illustrated in FIG. 2, the light source 34 is an array of LEDs or other energy sources. In another exemplary embodiment, the light source is an array of optical fibers powered by a laser. The apparatus of the invention also includes an energy source in power communication with the light source and is adapted to provide power to the light source. The energy source can be DC and/or AC. The housing of the apparatus can optionally be adapted to contain an autonomous energy source (e.g., batteries or the like). Alternatively, the energy source can be located outside of the housing, but is in power communication with the light source via any conventional means, including cable(s). The apparatus further includes a controller that controls the amount (including duration) of the light that is applied to the treated area.

One embodiment of the device and method of the invention involve use of arrays of light emitting diodes (LEDs), comprising at least one set of LEDs which emit light at the required wavelength. The set of LEDs is configured within the array in predetermined patterns, and is activated at the required frequency in sequence for predetermined durations of time. In certain aspects of the invention, treatments are provided involving inserting the limb into the device, adjusting for comfort, and activating the device for a pre-programmed treatment of approximately 5-45 minutes.

When a laser is utilized as a light source, the generated beam is controllably absorbed in the target tissue at the required depths.

Utilization of a laser in the present invention as a light source is accompanied by automatic target thermal feedback to precisely control the dosimetry of the laser, intense light or intense pulsed light irradiation. This is needed to prevent damage to surrounding tissue and reduces pain. For this purpose, a non-contact thermal detector can be provided. The output of the non-contact thermal detector is used to adjust the power output of the laser to maintain a selected treatment temperature at the treatment site.

In the invention, absorption of laser energy by the nail bed of the infected toe or finger results in a controlled elevation in temperature, to a temperature effective of disinfection at the infected regions or areas. In the invention, this occurs without causing irreversible thermal damage to the infected nails. The laser control system of the invention adjusts the energy to maintain a pre-selected target temperature at the spot. In one embodiment of the invention, to maximize patient comfort and safety, an optional continuous or pulsed cooling device can be provided to deliver a stream of coolant to the target treatment spot during or after each laser treatment session.

As best illustrated in FIGS. 1, 2, 3 and 4, energy or light source(s) 16 is disposed within front part of the apparatus in the vicinity of the treatment chamber 14, which is adapted to accommodate toes and toenails of a patient and additional energy or light sources to provide energy irradiation to all other skin areas.

To further control the treatment process, a sensor 32 is provided within the treatment chamber 14. The sensor 32 is capable of detecting the level of melanin, hemoglobin or water/moisture content, etc., within the skin of a patient positioned within the chamber. Thus, optimal levels of radiation can be achieved for each zone of treatment. For example, a higher level of radiation can be provided at the front area 15 of the treatment chamber 14 which accommodates toes and toenails infected with a fungus. On the other hand, lower levels of radiation will be generated and directed to the areas of the treatment chamber accommodating a heel and the surrounding regions of the foot. To further control the treatment a condition of the surrounding tissue is monitored by a detecting arrangement or detector 35 adopted to detect irradiation reflected from such tissue. One of the main functions of the detector 35 is to control the effect of the energy or light source on the surrounding tissue of a patient. In every individual case a doctor sets specific characteristics of the irradiation to produce the required effect. If situation in the treatment chamber become unfavorable, for example the temperature exceeds predetermined limits, the detector 35 generates a signal directed to the control unit 8 which in turn produces a correcting signal to the power unit or to the control arrangement 28 of the cooling system 22. This in turn energizes circulation pumps 37 and/or cooling plates 38, so as to directly and indirectly lower temperature in the treatment chamber 14. Similar signals can be also produced when the prearranged levels of the energy density, power density or other characteristics of the operating laser are attained. This is necessary to exclude possibility of damaging an adjacent healthy skin tissue. The detecting arrangement 35 can be made utilizing a wide variety of photoelements, photoresistors, photodiodes and similar devices.

In the embodiment of the invention illustrated in FIG. 2 a plurality of energy sources 34, such as an array of LEDs for example, are disposed within the walls of the treatment chamber formed within the hollow interior of the apparatus. Although the multiple energy sources can be randomly provided, in the illustrated embodiment such energy sources 34 are uniformly distributed through the inner surface of the treatment chamber.

In a further embodiment of the invention, the inner surface of the treatment chamber 14 is covered by a light reflective material. In this manner, the energy of the light sources disposed at the reflected layer are fully reflected and directed to the foot positioned within the treatment chamber 14.

According to still yet another embodiment of the invention, the inner area of the treatment chamber is covered by a plastic material impermeable to the aqueous solution, and transparent to light radiation generated by the energy/light sources. Thus, the plastic material forms a disposable envelope adapted to accommodate a foot of a patient and usable only during a specific treatment session arranged for a particular individual/patient. The envelope is removed from the apparatus upon completion of the treatment and properly disposed. Use of such disposable envelopes prevents transmission of fungus and other diseases from one patient to another.

According to an essential aspect of the invention, the refractive index of the aqueous solution and/or any other material or substance which is in contact with the skin surface of a patient, should match or to be substantially identical to the refractive index of the skin of the patient itself. The same principal is applicable to light sources used in the apparatus and the method of the invention. This means that the refractive index of a transparent light window surface (through which the light is irradiated by the light source) should match or be substantially identical to the refractive index of the material in contact with it and eventually with the skin surface of a patient.

In a still further embodiment of the invention, a pressure source can be provided within the treatment chamber 14. This embodiment is especially beneficial with the treatment chamber being formed with resilient walls or when the flexible plastic envelope 44 is used in the chamber. Thus, upon pressure being elevated, the resilient walls or the flexible envelope disposed within the treatment chamber closely surrounds the foot and the toes subjected to a treatment within the chamber. This arrangement makes the steps of applying the aqueous solution or irradiating the step of irradiation even more efficient.

According to the method of the invention, initially the foot partially submerged into an aqueous solution can be also subjected to a light radiation treatment. The level of the solution within the treatment chamber is periodically raised, so as to cover the entire surface of the foot. After completion of the treatment, the solution is removed into a reservoir or recycled; and the foot is dried by an air stream formed by a vacuuming air-pump which can be connected to the treatment chamber 14 through the exit tube 40.

The method of the present invention also includes the steps of irradiating the infected area with the light or energy sources 16, 34 at a wavelength absorbed by skin chloroforms including but not limited to melanin, hemoglobin, oxyhemoglobin, or water in the skin or nails of a patient, so as to destroy fungal and/or bacterial infection, and/or microbes, and/or coagulate contaminated or diseased tissue in the nail, under the nail, in the nail matrix or at any other affected area of the skin. Since light can penetrate through the skin and through the nail, the irradiating step is achieved by irradiating either directly or indirectly through the nail with a light source at the required wavelength, so as to destroy infected material on the nail bed as well as in the matrix below and around the nail bed.

In the method of the invention, the steps of treating the infected area by an aqueous solution and the step of irradiating the infective area with a light source can be conducted separately/independently of each other or in combination.

What is claimed is:

1. A method for treatment of one or more skin medical conditions of a limb of a patient, the skin medical conditions including a fungal infection, the method comprising:
    inserting the limb of said patient within a hollow treatment chamber formed within a shoe shaped housing, the shoe shaped housing having at least one light source configured to emit skin treatment light energy, a circulation assembly configured to circulate a skin treatment aqueous solution, one or more sensors, and a power and control unit to control the circulation assembly and the at least one light source;
    detecting one or more skin parameters of the limb with the one or more sensors, the skin parameters selected from the group consisting of skin melanin concentration, skin hemoglobin concentration, and skin water content;
    controlling with the power and control unit:
        a treatment protocol for the limb based on said one or more skin parameters detected by said one or more sensors, the treatment protocol including a duration of exposure of the limb to said aqueous solution and an amount of said skin treatment energy for irradiating the limb; and
        an amount of the skin treatment aqueous solution in the treatment chamber to partially or fully submerge the limb;
    submerging the limb or a portion thereof in said skin treatment aqueous solution by delivering the amount of skin treatment aqueous solution to the treatment chamber, with the circulation assembly;
    circulating the amount of the skin treatment aqueous solution within the treatment chamber with the circulation assembly for the duration of exposure; and
    irradiating said limb within the treatment chamber with the amount of skin treatment energy at a wavelength absorbed by the skin of the limb, with the at least one light source.

2. The method of claim 1, wherein the skin treatment aqueous solution is capable of eliminating skin pathogens.

3. The method of claim 1, wherein:
    the treatment chamber extends between front and rear areas of the housing;
    the housing further includes a supporting platform disposed within the hollow chamber with a top surface of the platform is positioned at an acute angle relative to a bottom of the apparatus;
    the treatment chamber is supported by the platform and angled having a front part at a lower level than a rear part thereof than a rear part of the treatment chamber; and
    wherein said step of inserting the limb of said patient comprises inserting a foot of a patient within said treatment chamber with nails of the foot disposed in said front part of said treatment chamber are lower than a heel of the foot disposed in said rear part of the treatment chamber.

4. The method of claim 3, wherein a top surface of the supporting platform is formed from a resilient material and a gel layer is provided below the resilient top surface of the platform, the method further comprising the step of adapting said resilient material to a specific shape of said foot of said patient.

5. The method of claim 3, wherein the treatment chamber includes an inner area covered by flexible material transparent to light radiation, the flexible material forming a disposable envelope positioned within the treatment chamber, and wherein said inserting said foot of said patient within said treatment chamber comprises covering said foot with said flexible material.

6. The method of claim 3, wherein said apparatus further comprises a cooling arrangement formed within the interior of the supporting platform and a solution reservoir, wherein the cooling arrangement and the interior of the treatment chamber form part of said circulation assembly, and said method further comprising the step circulating a cooling fluid within the treatment chamber thereby reducing a temperature of the aqueous solution.

7. The method of claim 6, wherein the apparatus further comprises a detecting arrangement selected from the group consisting of photoelements, photoresistors and photodiodes, and wherein the method further comprises the steps of:

using said detecting arrangement, detecting a predetermined condition within the treatment chamber;

when said predetermined condition is detected at said detecting arrangement generating a signal directed to the power and control unit; and responsive to receipt of said signal directed to said power and control unit, producing a correcting signal directed to the circulation assembly containing the cooling fluid for activation thereof to adjust the condition in the treatment chamber.

8. The method of claim 6, said cooling arrangement comprising a resilient light transparent pocket disposed at the front area of said treatment chamber and including a circulation loop containing a cooling fluid, and wherein said method further includes circulating said cooling fluid within said circulation loop of said light transparent pocket thereby to cool the nails and to improve transmission of laser irradiation energy to the nails.

9. The method of claim 1, wherein said irradiating comprises providing different levels of radiation for different zones of treatment based on results of said detecting at least one of a level of melanin, hemoglobin, and skin water content.

10. The method of claim 1, further comprising a step of cooling the treatment chamber with a cooling plate within the shoe shaped housing.

* * * * *